(12) United States Patent
Vic et al.

(10) Patent No.: US 7,186,274 B2
(45) Date of Patent: Mar. 6, 2007

(54) METHOD FOR TREATING HUMAN KERATIN FIBERS WITH ORGANOMODIFIED METALLIC PARTICLES

(75) Inventors: Gabin Vic, Venette (FR); Aude Livoreil, Paris (FR); Franck Giroud, Clichy (FR)

(73) Assignee: L'Oreal, Paris (FR)

( * ) Notice: Subject to any disclaimer, the term of this patent is extended or adjusted under 35 U.S.C. 154(b) by 165 days.

(21) Appl. No.: 10/393,924

(22) Filed: Mar. 24, 2003

(65) Prior Publication Data

US 2004/0010864 A1  Jan. 22, 2004

Related U.S. Application Data

(60) Provisional application No. 60/396,580, filed on Jul. 18, 2002.

(30) Foreign Application Priority Data

Apr. 8, 2002 (FR) .................................. 02 04354

(51) Int. Cl.
*A61K 7/13* (2006.01)
(52) U.S. Cl. .................. 8/405; 8/425; 8/428; 132/202; 132/208; 424/70.1; 424/70.4; 424/70.5; 424/70.6
(58) Field of Classification Search .................. 8/405, 8/425, 428; 132/202, 208; 424/70.1, 70.4, 424/70.5, 70.6
See application file for complete search history.

(56) References Cited

U.S. PATENT DOCUMENTS 5,720,805 A  2/1998  Wellinghoff et al.

5,744,245 A * 4/1998 Bishop ........................ 428/457

FOREIGN PATENT DOCUMENTS

DE   101 17 336    10/2002
WO   WO 01/68596   9/2001

OTHER PUBLICATIONS

Brust, M et al., Synthesis and reactions of functionalized gold nanoparticles, Journal of fhe Chemical society, Chemical communicaions (1995). (16) abstract.*
Brust, M et al., Synthesis of thiol-derived gold nanoparticles in a two-phase liquid-liquid system, Journal of the chemical Society, Chemical Communications (1994) (7) abstract.*
DATABASE WPI, Week 199518; Derwent Publications Ltd., London, GB; AN 1995-136093; XP002227914 & JP 07 060109 A (Mitsui Toatsu Chem. Inc.); Mar. 7, 1995.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The present invention relates to the use of organomodified metallic nanoparticles preferably bearing at their surface a self-assembled monolayer of organosulphur compounds. A preferred use is in suspension form for dyeing and/or treating human keratin fibers. The invention also relates to a process for dyeing and/or treating human keratin fibers, by the application to the keratin fibers of such a suspension, and also to compositions used to perform such a process. The invention includes the colouring and/or treating of human keratin fibers, in particular the hair, with the invention suspension. Compositions of the nanoparticles with cosmetic active principles, and uses thereof, also are described.

31 Claims, No Drawings

METHOD FOR TREATING HUMAN KERATIN FIBERS WITH ORGANOMODIFIED METALLIC PARTICLES

REFERENCE TO PRIOR APPLICATIONS

This application claims benefit of priority to U.S. provisional application 60/396,580, filed Jul. 18, 2002, and to French patent application 0204354 filed Apr. 8, 2002, both of which are incorporated herein by reference.

SUMMARY OF THE INVENTION

The present invention relates to the use of organomodified metallic nanoparticles preferably bearing at their surface a self-assembled monolayer of organosulphur compounds. A preferred use is in suspension form for dyeing and/or treating human keratin fibers. The invention also relates to a process for dyeing and/or treating human keratin fibers, comprising the application to the keratin fibers of such a suspension, and also to compositions used to perform such a process. The invention includes the colouring and/or treating of human keratin fibers, in particular the hair, with the invention suspension. Compositions of the nanoparticles with cosmetic active principles and uses thereof also make up a part of the invention.

BACKGROUND OF THE INVENTION

Patent application EP 1 064 918 describes the application, to the hair, of metallic nanoparticles suspended in a clear composition, in order to give treated hair a shiny appearance. The deposition of the nanoparticles is described as a physicochemical adsorption process which does not make it possible to obtain remanent deposits, i.e. deposits that withstand removal by shampooing.

The inventors have discovered that it is possible to increase the remanence of metallic nanoparticles at the surface of the hair and thus to maintain their cosmetic effect even after shampooing several times, by using not "naked" metallic nanoparticles, as described in EP 1 064 918, but organomodified nanoparticles, i.e. nanoparticles bearing organic groups at their surface.

DETAILED DESCRIPTION OF THE PREFERRED EMBODIMENTS

Useful organomodified nanoparticles have recently been synthesized and described, inter alia, in the following publications:

Synthesis and Characterization of Carboxylate-Modified Gold-Nanoparticle Powders Dispersible in Water, Langmuir, 1999, 15, 1075–1082.

Comparative Study of Dodecanethiol-Derivatized Silver Nanoparticles Prepared in One-Phase and Two-Phases Systems, Langmuir, 1998, 14, 226–230.

The metallic nanoparticles described in these publications are particularly useful in the present invention and are characterized in that they bear at their surface a monolayer of organosulphur compounds forming a structure commonly known as a self-assembled monolayer (see the article by A. Ulman, Chem. Rev., 1997, 96, 1533).

The inventors have also found that metallic particles thus "clad" with a monolayer of organic compounds are markedly easier to handle and to disperse in various liquid solvents for the purpose of preparing a cosmetic composition.

The diversity of organic groups that may be attached to the surface of the metallic nanoparticles makes it possible to provide several routes for immobilizing the particles at the surface of human keratin fibers, such as the fixing by covalent bonding or by adsorption of the organic groups of the self-assembled layer directly onto the keratin fiber, the fixing by covalent bonding or by adsorption of the organic groups of the self-assembled layer onto a film-forming polymer predeposited on the surface of the keratin fiber, the deposition of a mixture containing both the organomodified particles and a film-forming polymer, which may optionally be crosslinked in situ, the deposition on the keratin fibers of nanoparticles bearing functions capable of reacting together so as to form a layer of crosslinked material around the fiber, or alternatively, the deposition on the keratin fiber of organomodified metallic particles also coated with one or more layer(s) of polymer fixed by adsorption or by covalent bonding to the layer of self-assembled compounds, where combinations of these approaches may also be used.

All these immobilization routes exploit the diversity of the organic groups that may be fixed to the surface of the metallic particles. This diversity allows great freedom in modifying the various surface parameters, such as the electrical charge or the hydrophobic nature, and thus in modifying the forces of interaction with the cosmetic substrate (e.g., keratin) and of increasing in particular the remanence of the deposit of metallic particles.

Thus, one subject of the present invention is, consequently, the use of a suspension of organomodified metallic nanoparticles bearing at their surface a self-assembled monolayer of organosulphur compounds, in a cosmetically acceptable medium, for dyeing and/or treating human keratin fibers, and more particularly for improving the sheen of keratin fibers, for facilitating the shaping of keratin fibers, for protecting keratin fibers against sunlight and/or for conditioning keratin fibers.

Specifically, the fixing of organomodified metallic nanoparticles to the hair may afford a certain number of cosmetic effects such as coloration and non-greasy sheen. Moreover, a styling effect due to the modification of the surface state of the hairs (roughness, surface charge) is provided. By virtue of their reflective properties, the metallic particles will also be capable of protect the hair against the harmful effects of sunlight. The organomodified metallic nanoparticles also make it possible to condition the keratin fibers.

Another subject of the invention is a process for dyeing and/or treating human keratin fibers, comprising the application to the keratin fibers of a suspension of organomodified metallic nanoparticles bearing at their surface a self-assembled monolayer of organosulphur compounds, in a cosmetically acceptable medium.

As indicated above, there are a large number of routes for immobilizing the organomodified metallic nanoparticles on keratin fibers, in other words a large number of application processes, which will be described in detail hereinbelow as different embodiments of the invention.

In a first embodiment of the process of the invention, the organomodified metallic nanoparticles are fixed directly to the keratin fibers by covalent bonding between functions borne by the particles and functions borne by the keratin.

The residues of organosulphur compounds fixed to the surface of the nanoparticles preferably correspond to the formula

—S—R—R$^1$ in which

R represents a spacer arm selected from the group consisting of linear, branched or cyclic, saturated or unsaturated C$_{1-190}$ divalent carbon-based chains, optionally interrupted with hetero atoms such as sulphur, oxygen, nitrogen, silicon or phosphorus, and optionally bearing one or more substituents such as hydroxyl, amine, thiol, carbamate, ether, acid, ester, amide, cyano or ureido groups, R$^1$ represents an organic function capable of reacting with the keratin fibers, and the suspension of organomodified nanoparticles is applied directly to the keratin fibers under conditions allowing the covalent bonding of the nanoparticles by reaction of the function R$^1$ with the keratin, and more particularly with the hydroxyl, primary and secondary amine, thiol and carboxylic acid functions borne by the side groups of the residues of the amino acids of the keratin.

R as defined above preferably represents a linear C$_{1-50}$ and in particular C$_{4-20}$ alkylene group.

In a second embodiment of the process of the invention, the particles are also fixed via covalent bonding, but in contrast with the first embodiment, not directly to the keratin but to a film-forming polymer predeposited onto the fiber, which acts as a "primer" for attaching the particles.

In this embodiment, the process comprises at least two steps:

a first step of depositing on the keratin fibers a film-forming polymer comprising reactive functions selected from the group consisting of, for example, hydroxyl, primary and secondary amine, thiol, carboxylic acid and carboxylic anhydride functions, and a second step of applying to the keratin fibers surrounded with the said film-forming polymer a suspension of organomodified metallic nanoparticles bearing at their surface a self-assembled monolayer of organosulphur groups of formula

—S—R—R$^1$ in which

R has the meaning and the preferred meaning indicated above, and R$^1$ represents an organic function capable of reacting with the, e.g., hydroxyl, primary and secondary amine, thiol, carboxylic acid and carboxylic anhydride reactive functions of the said film-forming polymer, under conditions allowing the covalent bonding of the nanoparticles by reaction between the function R$^1$ and the functions of the said film-forming polymer.

There are a large number of organic functions capable of reacting with the active-hydrogen-containing functions of keratin or of the film-forming polymer predeposited on the hair. A person skilled in the art, in view of this disclosure, is able to use these functions and their reaction mechanism (substitution, addition to a double or triple bond, ring opening, etc.) for producing a covalent bond, and will also be able to select reaction conditions that are suitable for establishing a covalent bond (temperature, pH, application of radiation, presence of a chemical or biochemical coreagent or catalyst) without undue effort.

Examples of functions R$^1$ that may be mentioned include the following: epoxide, aziridine, vinyl, acrylonitrile, (meth)acrylic acid, alkyl (meth)acrylate, crotonic acid, cinnamic acid and alkyl cinnamate, styrene, butadiene, vinyloxy, vinyl ketone, alkyl maleate, maleimides, vinylsulphone, carboxylic acid, carboxylic acid chloride, carboxylic anhydride, alkyl carboxylate, acetal, hemiacetal, aminal, hemiaminal, ketone, α-hydroxy ketone, α-halogen ketone, lactone, thiolactone, isocyanate, thiocyanate, imine, imide (succinimides or glutimides), N-hydroxysuccinimide ester, imidate, oxazine, oxazoline, oxazinium, oxazolinium, alkyl, aryl or aralkyl halides, halide of an unsaturated carbocycle or heterocycle (for example chlorotriazine, chloropyrimidine, chloroquinoxaline or chlorobenzotriazole), sulphonyl halide, siloxane, silane, hydrazine, phenylglyoxal, aldehyde, azlactone, imido ester, thiosulphate, diazirine, pyridylthio, primary and secondary amine, and phenyl azide.

The predeposited film-forming polymer comprising reactive functions may be chosen, for example, from polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, polymers derived from maleic, fumaric and/or itaconic acid or anhydride, and polyamidoamines. Among these polymers, the ones particularly preferred are cationic polymers such as polyethyleneimines and polylysines, on account of their excellent affinity for the keratin substrate which has an anionic overall charge.

In the second embodiment of the process of the invention described above, it may, of course, also be envisaged for the functions described above for R$^1$ to be borne, not by the organosulphur compounds of the self-assembled layer, but by the predeposited film-forming polymer, and for R$^1$ then to represent a function capable of reacting with the functions of the polymer.

In a third and fourth embodiment of the process of the present invention, the metallic particles are fixed not via covalent bonds but via physicochemical adsorption onto the keratin substrate. Adsorption is defined as a phenomenon due to the weak interactions involving bonding energies of less than 50 kcal/mol. The bonding forces cover, for example, ionic interactions, the van der Waals forces, the hydrophobic interaction and the hydrogen bonds.

In concrete terms, in a third embodiment of the process of the present invention, the organosulphur groups correspond to the formula

—S—R—R$^2$ in which

R has the same meaning and preferred meaning as above, R$^2$ represents an organic function capable of establishing weak interactions with the keratin fibers, and the suspension of organomodified nanoparticles is applied directly to the keratin fibers under conditions allowing the adsorption of the nanoparticles by weak interaction between the function R$^2$ and the surface of the hair.

Needless to say, it is also possible to envisage, by analogy with the immobilization via covalent bonding (embodiments 1 and 2), that the adsorption of the particles via the functions R$^2$ takes place not directly on the keratin of the hair, but on a polymer predeposited onto the said hair. Consequently, a fourth process for dyeing and/or treating human keratin fibers comprises a first step of depositing on the keratin fibers a film-forming polymer, and a second step of applying to the keratin fibers surrounded with the said film-forming polymer a suspension of organomodified metallic nanoparticles bearing at their surface a self-assembled monolayer of organosulphur groups of formula

—S—R—R² in which R and R² have the same meaning as above, under conditions that allow the establishment of weak interactions between the group R² and the said predeposited film-forming polymer.

A very large number of film-forming polymers and of functions R² capable of establishing weak interactions with the said film-forming polymer are available.

Examples of functions R² that may be mentioned include the groups derived from a compound selected from the group consisting of carboxylic acids and salts thereof, primary, secondary, tertiary or quaternary amines, phosphates, oxygen-containing sulphur compounds such as sulphones, sulphonic acids, sulphoxides and sulphates, fullerenes, carbon nanotubes, carbocyclic or heterocyclic aromatic compounds, pyrenes, stilbenes, ferrocenes, carbazoles, ureidopyrimidone, melamine, cyanuric acid, phthalohydrazides, isoguanine, glycoluril, uracil, acylaminopyridine, thymine, guanine, cytidine, adenine and pterine.

The film-forming polymers that may be used in this process are the same as those mentioned above.

This fourth embodiment of the process of the invention also covers a particular method of bonding known, especially in the biochemical field, as "affinity" binding. This involves a more or less specific, reversible interaction between a ligand and a biological receptor. Examples of such ligand-receptor couples that may be mentioned include the following: biotin/avidin, antibody, antigen, lectins/oligosaccharide, complementary strands of DNA.

When applied to the embodiment described above, one of the partners, i.e. either the ligand or the receptor, will be borne by the polymer and the other will correspond to the function R² borne by the self-assembled organosulphur compounds at the surface of the metallic particles.

In a fifth embodiment of the process of the present invention, the metallic particles coated with a self-assembled monolayer of organic compounds are deposited onto the keratin fibers at the same time as a film-forming polymer. After evaporating off the suspension medium, the dried film contains the organomodified nanoparticles incorporated into and retained by the polymer film.

In this embodiment, the suspension of organomodified metallic nanoparticles thus also contains at least one film-forming polymer in dissolved or dispersed form in the cosmetically acceptable medium. The polymers that are suitable are identical to those given above for the fourth process. They preferably have a cationic overall charge, which gives them good affinity for keratin.

A particular variant of this embodiment may also be envisaged, in which the film-forming polymer is crosslinked in situ after deposition by means of reactive functions borne by the polymer for example double bonds, or by a suitable crosslinking agent present in the starting suspension or applied thereafter. Such a crosslinked polymer coat containing the organomodified metallic nanoparticles will show particularly good resistance to removal by washing the hair.

Another possibility for forming a remanent crosslinked coat containing organomodified metallic nanoparticles consists in using nanoparticles capable of establishing between themselves covalent bonds by reaction of reactive functions borne by the organosulphur compounds self-assembled into a monolayer at the surface of the particles.

In a sixth embodiment of the process of the invention, the organosulphur compounds consequently bear functions capable of reacting together so as to form around the fiber, during the evaporation of the solvent medium, a layer of crosslinked material.

Examples of such functions that may be mentioned include reactive silanes such as halosilanes or alkoxysilanes, siloxanes, thiols, or alternatively acrylic or vinyl double bonds that may be polymerized in the presence of a suitable initiator. The deposit obtained will be water-insoluble and will show good resistance to shampooing, which ensures good durability of the cosmetic effects afforded by this deposit.

A seventh embodiment of the process of the invention comprises applying to the hair metallic nanoparticles organomodified with a self-assembled monolayer of organosulphur compounds, and which are also coated with one or more layer(s) of identical or different organic polymer(s). This polymer may be simply adsorbed onto the surface of the organomodified nanoparticles, or it may be fixed via covalent bonding to the self-assembled organosulphur compounds.

The fixing via covalent bonding of the organic polymer may be obtained in a manner similar to that described for the second embodiment of the process, i.e. by reaction between functions R¹ borne by the particles and reactive functions borne by the polymer.

It is also possible to perform a free-radical copolymerization of the organomodified metallic particles bearing epoxide groups or vinyl or acrylic double bonds, preferably acrylic double bonds, with one or more vinyl or acrylic comonomers or comonomers of epoxide type. The organomodified nanoparticles may also function as free-radical initiator for the polymerization reaction, which will thus be incorporated into the macromolecular chain.

A person skilled in the art is familiar with the various polymerization processes for performing such a polymerization and mention will simply be made, as a preferred example of such a process, of the atom-transfer radical polymerization (ATRP) described, for example, in the article "*Controlled Synthesis of Crosslinked Ultrathin Polymer Films by Using Surface-Initiated Atom Transfer Radical Polymerization*", published in *Angew. Chem., Int. Ed.,* 2001, 40, 12510–12512.

The encapsulation described in the article is obtained by free-radical polymerization initiated with disulphides which form the self-assembled monolayer (SAM). Such a process allows particles having a structure of metallic core/organic shell type to be obtained. The thickness of the shell is generally between 2 nm and 300 nm.

Mention may be made, as a preferred disulphide free-radical initiator capable of forming self-assembled monolayers, of the compound of formula (BrC(CH₃)₂COOH(CH₂)₁₁S)₂ and, as a preferred monomer, of ethylene glycol dimethacrylate. Gold or silver nanoparticles will preferably be used.

The adjective "metallic" used in the present invention to describe the organomodified nanoparticles means
either that the nanoparticles are 100% of one or more metals in elemental form,
or that the nanoparticles comprise a surface layer (shell) of 100% of one or more metals in elemental form, and which surrounds a core, or heart, comprising a different material. Such nanoparticles with a core/shell structure will be described in greater detail hereinbelow.

The metals forming the organomodified metallic nanoparticles are preferably selected from the group consisting of alkali metals, alkaline-earth metals, transition metals and rare-earth metals, and alloys of these metals. It is particularly preferred to use aluminium, copper, cadmium, selenium, silver, gold, indium, iron, platinum, nickel, molybdenum, silicon, titanium, tungsten, antimony, palladium, zinc and tin, and alloys of these metals, and most particularly among these gold, silver, palladium, platinum, cadmium and selenium, and alloys of combinations of any and all these metals.

The organomodified metallic nanoparticles used in the present invention may especially be prepared according to the following two synthetic processes:

Process 1: One or more thiol compounds of general formula $R^1$—R—SH is (are) directly added to a metal salt, such as $HAuCl_4.3H_2O$ or $AgNO_3$, in suspension or in solution in an aqueous or organic medium, followed by reduction of the said metal salt by addition of a reducing agent such as sodium borohydride, sodium thiosulphate or trisodium citrate. Such a process is described, for example, in the article entitled "Synthesis and Characterization of Carboxylate-Modified Gold Nanoparticle Powders Dispersible in Water", Langmuir, 1999, 15, 1075–1082.

Process 2: A suspension of metallic nanoparticles is incubated in a solution of thiolates and/or of thiols and/or of disulphides and/or of thioethers and/or of xanthates and/or of thiocarbamates and/or of thiosulphates and/or of thiolactones to form a monolayer by chemisorption of the thiol derivatives onto the surface of the nanoparticles.

The monolayer of thiol compounds may then optionally be modified by exchange reaction with new thiol derivatives to form a new layer of different composition,
polymerization reaction using the chemical functions present at the end of the adsorbed thiol compounds forming the self-assembled monolayer,
nucleophilic and electrophilic substitution reaction,
free-radical substitution reaction,
addition reaction to a carbon-carbon or carbon-hetero atom multiple bond,
elimination reaction,
oxidation reaction.

Examples of such modifications to the chemical structure of the self-assembled monolayer are described, for example, in the article by R. Murray, Ace. Chem. Res., 2000, 33, pages 27–36.

As indicated above, the metallic nanoparticles used in the present invention also cover composite nanoparticles of core/shell type, with a metallic shell surrounding a core of a material preferably other than a metal in elemental form. The core of such nanoparticles may comprise a mineral or organic material. When it is a mineral material, it is preferably selected from the group consisting of the oxides, oxide dihydrates, hydroxides, carbonates, sulphides, silicates and phosphates of silicon, calcium, magnesium, zinc, aluminium, titanium, zirconium or cerium, micas and nacres.

When it is an organic material, it is preferably an organic polymer selected from the group consisting of styrene homopolymers and copolymers, polyorganosiloxanes, fluoro polymers, copolymers of ethylene and of vinyl acetate, polyvinyl alcohols, poly(ethylene oxide), polyvinylpyrrolidone, homopolymers and copolymers based on (meth)acrylic acid and/or on alkyl (meth)acrylates, polyurethanes, polyamides, polycarbonates, poly(vinyl chloride), poly(vinyl acetate), polypropylene, polyethylene, polyisobutylene, poly(1-butenylene), cellulose ethers, organic esters of cellulose, carboxyalkylcelluloses, cellulose sulphates, dextran sulphates and dextran ethers. These organic polymers forming the core of the metallic nanoparticles may be crosslinked using suitable crosslinking agents chosen as a function of the polymer. Examples of such crosslinking agents that may be mentioned include divinylbenzene, glutaraldehyde, 1,4-bis(acyloyl)piperazine, carbodiimides, N-hydroxysuccinimide, divinyl sulphone, dithiobis(succinimidyl) propionate and N-succinimidyl-3-(2-pyridyldithio) propionate.

The organomodified metallic nanoparticles according to the present invention for colouring and/or treating keratin fibers have intrinsic colouring properties that depend not only on the nature of the metal and of the organosulphur compounds forming the self-assembled monolayer, but also on the size of the particles. These colouring properties may be modified by grafting groups that absorb visible or UV light, derived from known organic dyes. These non-ionic, cationic, anionic or amphoteric organic dyes are chosen, for example, from nitrobenzene dyes, aminobenzene dyes, azo dyes, naphthoquinone, benzoquinone or anthraquinone dyes, dyes of aromatic diamine type, aminophenols, phenolic and naphtholic dyes, porphyrins such as tetraphenylporphyrins and metalloporphyrins, phthalocyanins, carotenoids, flavonoids and various fluorescent molecules such as fluorescein, rhodamine and coumarin.

The possibility of providing human keratin fibers with a particular colour and/or a particular cosmetic effect by means of fixing organomodified metallic nanoparticles, for example according to the various embodiments of the process of the present invention, is found to be particularly advantageous in combination with known cosmetic hair treatments, such as permanent reshaping, oxidation dyeing or bleaching of the hair.

The process of the present invention, carried out before or after the various steps of such processes, can thus improve the efficacy of the treatments or afford a particular cosmetic effect, which is especially adapted to the desirable or undesirable chemical and/or physical modifications resulting from these treatments.

Consequently, a subject of the present invention is also a pretreatment or post-treatment process for human keratin fibers, comprising performing the process according to the present invention before or after an oxidation-dyeing, reducing, bleaching, permanent-waving, styling or straightening treatment of the keratin fibers.

A subject of the present invention is also a cosmetic composition comprising, in a cosmetically acceptable medium,
at least one cosmetic active principle, and
organomodified metallic nanoparticles bearing at their surface a self-assembled monolayer of organosulphur compounds, as described above.

The cosmetic compositions of the present invention preferably contain from 0.0001% to 50% by weight, in particular from 0.01% to 5% by weight and ideally from 0.05% to 2% by weight of organomodified metallic nanoparticles, based on total weight.

The cosmetic active principles present in the cosmetic compositions of the present invention may be chosen, for example, from vitamins, saccharides, oligosaccharides, hydrolysed or non-hydrolysed, modified or unmodified polysaccharides, amino acids, oligopeptides, peptides, hydrolysed or non-hydrolysed, modified or unmodified proteins, polyamino acids, enzymes, branched or unbranched fatty acids and fatty alcohols, animal, plant or mineral waxes, ceramides and pseudoceramides, hydroxylated organic acids, UV screening agents, antioxidants and free-radical scavengers, chelating agents, antidandruff agents, seborrhoea regulators, calmants, cationic surfactants, cationic polymers, amphoteric polymers, optionally organomodified silicones, mineral, plant or animal oils, polyisobutenes and poly(α-olefins), fatty esters, anionic polymers in dissolved or dispersed form, nonionic polymers in dissolved or dispersed form, reducing agents, hair dyes or pigments, and mixtures thereof.

The cosmetic active principle is preferably present in a proportion of from 0.001% to 50% by weight, in particular from 0.01% to 20% by weight and ideally from 0.1% to 10% by weight, relative to the total weight of the cosmetic composition.

The cosmetically acceptable medium may comprise, consist of, or consist essentially of water and/or one or more cosmetically acceptable organic solvents such as lower alcohols, for instance ethanol, $C_{5-20}$ alkanes, acetone, methyl ethyl ketone, methyl acetate, ethyl acetate, butyl acetate, dimethoxyethane, polyols, polyol ethers, diethoxyethane and volatile silicones.

The cosmetic compositions of the present invention may be in any form, preferably a form allowing a uniform application of a sufficient amount of nanoparticles to keratin fibers. They may be rinse-out or leave-in compositions, and especially lotions, aerosol sprays, mousses, gels, shampoos or conditioners.

Needless to say, in addition to the cosmetically acceptable medium, one or more cosmetic active principle, and organomodified metallic nanoparticles, the cosmetic compositions may optionally contain one or more formulation adjuvants chosen, for example, from thickeners, pH adjusting and fixing agents, preserving agents, antifoams, fragrances and non-cationic surfactants. When the composition is in aerosol form, it also contains, of course, one or more propellants such as air, carbon dioxide, nitrogen, dimethyl ether and optionally halogenated hydrocarbons.

The invention will be illustrated with the aid of the examples that follow.

EXAMPLE 1

Synthesis of Gold Nanoparticles Coated with a Self-Assembled Monolayer of Compounds Containing Carboxylic Functions An aqueous solution containing 5% (196 mg in 4 g of water) of $HAuCl_4.3H_2O$ from Aldrich is prepared. An alcoholic solution of mercaptosuccinic acid is prepared by dissolving 187 mg (1.25 mmol) of mercaptosuccinic acid (Aldrich) in 100 ml of methanol. The two solutions are mixed together at room temperature with vigorous stirring using a magnetic stirrer. 189 mg of sodium borohydride (Aldrich) are then dissolved in 25 ml of water. This solution is added slowly, at a rate of 5 ml/minute, to the mixture indicated above. Stirring is then continued for one hour at room temperature. The suspension thus obtained is centrifuged for 5 minutes at 9 840×g. The supernatant is discarded and the pellet is taken up in 100 ml of an 80/20 methanol/water mixture. This suspension is subjected for 5 minutes to ultrasound emitted by a probe. The centrifugation/resuspension cycle is repeated twice with an 80/20 methanol/water mixture, and then a third time with pure methanol. The solid (pellet) is finally taken up in 100 ml of ethanol, which is evaporated off under vacuum using a rotary evaporator at a temperature of 35° C. and at a reduced pressure of 20 mbar. A finely dispersed brown powder is thus obtained.

The carboxylated metallic nanoparticles are dispersible in water or in water/alcohol mixtures and give a dark brown/black colloidal solution.

Quantitative Elemental Analysis by ESCA (Elemental Spectroscopy for Chemical Analysis)

10 mg of the carboxylated metallic nanoparticles prepared above are dispersed in 3 ml of an alcoholic 10% solution and 200 μl of this suspension are placed on a crystal of silicon having a surface area of 1 $cm^2$. After evaporating off the solvent, the sample is analysed in a VG ESCALAB MkII analyser. Scans are acquired on the peaks corresponding to Au $4f^{7/2}$, C1s, O1s and S2s at a constant energy of 20 eV.

The elemental analysis reveals the following contents (in atom %) for the various elements below:

Au:2.41% ; O:16.84% ; C:79.82%; S:0.77% and Na:0.16.

These results thus clearly confirm the expected presence of gold, sulphur and carbon in the nanoparticles analysed.

Determination of the Particle Size by Transmission Electron Microscopy (TEM)

The organomodified metallic nanoparticles are suspended in a 10% alcoholic solution with agitation by ultrasound. One drop of this solution is placed on a carbon grille. The nanoparticles are observed at 400 kV with a Jeol 4000 EX (II) high-resolution electron microscope with a resolution of 0.16 nm. Several zones which were observed at a magnification of 400 000 show particles of between 1.25 and 6.35 nm in size with a mean size equal to 3.75 nm.

EXAMPLE 2

Fixing of the Carboxylated Nanoparticles Directly onto the Keratin Fibers 85 mg of pieces of grey hair (200 μm long) are washed with 1 ml of shampoo in a 1.5 ml Eppendorf tube. After centrifugation, the supernatant is removed and the hair pellet is rinsed twice with 1 ml of distilled water. 1 ml of an aqueous suspension of the carboxylated nanoparticles prepared in Example 1 (5.2 mg/ml) is then added and the mixture is stirred for 1 hour at room temperature. After centrifugation, the supernatant is removed and rinsing is performed 3 times with 1ml of a shampoo solution, and then a further 3 times with distilled water. The hair is then dried for 12 hours at 45° C.

The pieces of hair thus treated have a pronounced black colour that is remanent with respect to shampooing.

Given that the very small size of the nanoparticles does not allow a direct detection by scanning electron microscopy (SEM), the deposit is first treated with a solution sold by the company Sigma under the name Silver Enhancer SE-100, which enables the size of the particles to be increased by further deposition of silver on their surface.

The scanning electron microscopy and the EDX analysis clearly show the presence of gold nanoparticles at the surface of the pieces of hair.

EXAMPLE 3

Fixing of Carboxylated Nanoparticles by Adsorption onto Keratin Fibers Coated with Polyethyleneimine 85 mg of pieces of grey hair (200 μm long) are washed with 1 ml of shampoo in a 1.5 ml Eppendorf tube. After centrifugation, the supernatant is discarded and the hair pellet is rinsed twice with 1 ml of distilled water. The hair is then incubated for 1 hour at room temperature in the presence of 1 ml of an aqueous solution containing 5% polyethyleneimine (sold by the company Bayer under the name LUPAZOL®). At the end of this incubation, the mixture is centrifuged, the supernatant is discarded and rinsing is performed twice with 1 ml of distilled water. 1 ml of an aqueous suspension of the carboxylated nanoparticles prepared in Example 1 (5.2 mg/ml) is then added to the hair pellet, and the mixture is stirred for 4 hours at room temperature. After centrifugation, the supernatant is discarded and rinsing is performed 3 times with 1 ml of a shampoo solution and then a further 3 times with distilled water. The hair is then dried for 12 hours at 45° C.

The pieces of hair thus obtained have a pronounced black colour that is remanent with respect to shampooing.

The scanning electron microscopy and EDX analysis after treatment with a solution of Silver Enhancer SE-100 (Sigma) confirm the presence of gold nanoparticles on the surface of the hair.

EXAMPLE 4

Fixing of Carboxylated Nanoparticles by Chemical Grafting onto Keratin Fibers Coated with Polyethyleneimine 85 mg of pieces of grey hair (200 µm long) are washed with 1 ml of shampoo in a 1.5 ml Eppendorf tube. After centrifugation, the supernatant is discarded and the hair pellet is rinsed twice with 1 ml of distilled water. The hair is then incubated for 1 hour at room temperature in the presence of 1 ml of an aqueous solution containing 5% polyethyleneimine (sold by the company Bayer under the name LUPAZOL®). At the end of this incubation, the mixture is centrifuged, the supernatant is discarded and rinsing is performed twice with 1 ml of distilled water. 28 mg of 1-ethyl-3-(3-dimethylaminopropyl)carbodiimide (EDC) and 20 mg of N-hydroxysuccinimide (NHS) are added to 1 ml of a suspension of carboxylated gold nanoparticles (5.5 mg/ml) in a pH 4.7, 0.1 M MES buffer. The solution is stirred for 1 minute at room temperature and then added to the rinsed hair pellet. The suspension obtained is stirred for 4 hours at room temperature and centrifuged, the supernatant is discarded and rinsing is performed three times with 1 ml of a shampoo solution and then 3 times with 1 ml of distilled water. The hair is then dried for 12 hours at 45° C.

The pieces of hair thus treated have a pronounced black colour that is remanent with respect to shampooing.

After treatment with a solution of Silver Enhancer S-100 (Sigma), the hair is analysed by scanning electron microscopy and by EDX.

The above written description of the invention provides a manner and process of making and using it such that any person skilled in this art is enabled to make and use the same, this enablement being provided in particular for the subject matter of the appended claims and including the use of a suspension of organomodified metallic nanoparticles bearing at their surface a self-assembled monolayer of organosulphur compounds, in a cosmetically acceptable medium, for dyeing and/or treating human keratin fibers, particularly for improving the sheen of keratin fibers, for facilitating the shaping of keratin fibers, for protecting keratin fibers against sunlight and/or conditioning keratin fibers. Similarly fully described and enabled is a process for dyeing and/or treating human keratin fibers, comprising the application to the keratin fibers of a suspension of organo-modified metallic nanoparticles bearing at their surface a self-assembled monolayer of organosulphur compounds, in a cosmetically acceptable medium. Further fully described and enabled is a pretreatment or post-treatment process for human keratin fibers, comprising performing a dyeing and/or treatment process according to the invention before or after an oxidation dyeing, reducing, bleaching, permanent-waving, styling or straightening treatment, respectively.

The written description above also fully describes and enables a cosmetic composition comprising, in a cosmetically acceptable medium,
at least one cosmetic active principle, and
organomodified metallic nanoparticles bearing at their surface a self-assembled monolayer of organosulphur compounds.

Preferred embodiments of the invention fully described and enabled include:

A method for dyeing and/or treating human keratin fibers, comprising applying thereto a suspension of organomodified metallic nanoparticles bearing a self-assembled monolayer of organosulphur compounds on a surface thereof in a cosmetically acceptable medium, and A composition comprising, in a cosmetically acceptable medium,
at least one cosmetic active principle, and
organomodified metallic nanoparticles bearing a self-assembled monolayer of organosulphur compounds on a surface thereof.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

What is claimed is:

1. A method for dyeing and/or treating human keratin fibers, comprising applying to the human keratin fibers, a suspension of organomodified metallic nanoparticles bearing a self-assembled monolayer of organosulphur groups on a surface thereof in a cosmetically acceptable medium, wherein the metallic portion is selected from the group consisting of gold, silver, palladium, platinum, cadmium, and alloys of these metals.

2. The method according to claim 1, wherein said method is a method of treating, and wherein said method improves the sheen of keratin fibers, facilitates the shaping of keratin fibers, protects keratin fibers against sunlight, or conditions keratin fibers.

3. The method according to claim 1, wherein said method is a method of dyeing.

4. The method according to claim 1, wherein said organosulphur groups are fixed to the surface of the nanoparticles, and correspond to the formula

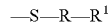

$$-S-R-R^1$$

in which

R represents a spacer arm selected from the group consisting of linear, branched or cyclic, saturated or unsaturated $C_{1-100}$ divalent carbon-based chains, optionally interrupted with hetero atoms and optionally bearing one or more substituents and $R^1$ represents an organic function capable of reacting with the keratin fibers, and wherein the suspension of organomodified nanoparticles is applied directly to the keratin fibers under conditions allowing the covalent bonding of the nanoparticles by reaction of the function $R^1$ with the keratin.

5. The method according to claim 1, further comprising depositing a film-forming polymer comprising reactive functions selected from the group consisting of hydroxyl, primary and secondary amine, thiol, carboxylic acid and carboxylic anhydride functions on the keratin fibers, prior to applying the suspension of organomodified metallic nanoparticles to keratin fibers, the organosulphur groups having the formula

—S—R—R$^1$ in which

R represents a spacer arm selected from the group consisting of linear, branched or cyclic, saturated or unsaturated $C_{1-100}$ divalent carbon-based chains, optionally interrupted with hetero atoms and optionally bearing one or more substituents, and R$^1$ represents an organic function capable of reacting with reactive functions of the film-forming polymer, under conditions allowing the covalent bonding of the nanoparticles by reaction between the function R$^1$ and the reactive functions of the said film-forming polymer.

6. The method according to claim 4, wherein R$^1$ represents a function selected from the group consisting of: epoxide, aziridine, vinyl, acrylonitrile, (meth)acrylic acid, alkyl (meth)acrylate, crotonic acid, cinnamic acid and alkyl cinnamate, styrene, butadiene, vinyloxy, vinyl ketone, alkyl maleate, maleimides, vinylsulphone, carboxylic acid, carboxylic acid chloride, carboxylic anhydride, alkyl carboxylate, acetal, hemiacetal, aminal, hemiaminal, ketone, α-hydroxy ketone, α-halo ketone, lactone, thiolactone, isocyanate, thiocyanate, imine, imide, N-hydroxysuccinimide ester, imidate, oxazine, oxazoline, oxazinium, oxazolinium, alkyl, aryl or aralkyl halides, halide of an unsaturated carbocycle or heterocycle, sulphonyl halide, siloxane, silane, hydrazine, phenylglyoxal, aldehyde, azlactone, imido ester, thiosulphate, diazirine, pyridylthio, primary and secondary amine, and phenyl azide.

7. The method according to claim 5, wherein R$^1$ represents a function selected from the group consisting of: epoxide, aziridine, vinyl, acrylonitrile, (meth)acrylic acid, alkyl (meth)acrylate, crotonic acid, cinnamic acid and alkyl cinnamate, styrene, butadiene, vinyloxy, vinyl ketone, alkyl maleate, maleimides, vinylsulphone, carboxylic acid, carboxylic acid chloride, carboxylic anhydride, alkyl carboxylate, acetal, hemiacetal, aminal, hemiaminal, ketone, χ-hydroxy ketone, χ-halo ketone, lactone, thiolactone, isocyanate, thiocyanate, imine, imide, N-hydroxysuccinimide ester, imidate, oxazine, oxazoline, oxazinium, oxazolinium, alkyl, aryl or aralkyl halides, halide of an unsaturated carbocycle or heterocycle, sulphonyl halide, siloxane, silane, hydrazine, phenylglyoxal, aldehyde, azlactone, imido ester, thiosulphate, diazirine, pyridylthio, primary and secondary amine, and phenyl azide.

8. The method according to claim 5, wherein said film-forming polymer comprising reactive functions is selected from the group consisting of polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, polymers derived from maleic, fumaric and/or itaconic acid or anhydride polymers, and polyamidoamines.

9. The method according to claim 1, wherein the organosulphur groups correspond to the formula

—S—R—R$^2$ in which

R$^1$ represents a spacer arm selected from the group consisting of linear, branched or cyclic, saturated or unsaturated $C_{1-100}$ divalent carbon-based chains, optionally interrupted with hetero atoms and optionally bearing one or more substituents, and R$_2$ represents an organic function capable of establishing weak interactions with the keratin fibers, and wherein the suspension of organomodified nanoparticles is applied directly to the keratin fibers under conditions allowing the adsorption of the nanoparticles by weak interaction between the function R$_2$ and the surface of the fibers.

10. The method according to claim 1, further comprising depositing a film-forming polymer on the keratin fibers prior to applying a suspension of organomodified metallic nanoparticles to the keratin fibers, the nanoparticles bearing at their surface a self-assembled monolayer of organosulphur groups of formula

—S—R—R$^2$ in which

R represents a spacer arm selected from the group consisting of linear, branched or cyclic, saturated or unsaturated $C_{1-100}$ divalent carbon-based chains, optionally interrupted with hetero atoms and optionally bearing one or more substituents, and R$^2$ represents an organic function capable of establishing weak interactions with the film-forming polymer, under conditions that allow the establishment of weak interactions between R$^2$ and the film-forming polymer.

11. The method according to claim 9, wherein R$^2$ represents a radical selected from the group consisting of radicals of carboxylic acids and salts thereof, primary, secondary, tertiary or quaternary amines, phosphates, oxygen-containing sulphur compounds, fullerenes, carbon nanotubes, carbocyclic or heterocyclic aromatic compounds, pyrenes, stilbenes, ferrocenes, carbazoles, ureidopyrimidone, melamine, cyanuric acid, phthalohydrazides, isoguanine, glycoluril, uracil, acylaminopyridine, thymine, guanine, cytidine, adenine and pterine.

12. The method according to claim 10, wherein R$^2$ represents a radical selected from the group consisting of radicals of carboxylic acids and salts thereof, primary, secondary, tertiary or quaternary amines, phosphates, oxygen containing sulphur compounds, fullerenes, carbon nanotubes, carbocyclic or heterocyclic aromatic compounds, pyrenes, stilbenes, ferrocenes, carbazoles, ureidopyrimidone, melamine, cyanuric acid, phthalohydrazides, isoguanine, glycoluril, uracil, acylaminopyridine, thymine, guanine, cytidine, adenine and pterine.

13. The method according to claim 10, wherein the film-forming polymer is selected from the group consisting of polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, and polyamidoamines.

14. The method according to claim 1, wherein the suspension of organomodified metallic nanoparticles further comprises at least one film-forming polymer in dissolved or dispersed form in the cosmetically acceptable medium.

15. The method according to claim 14, wherein the film-forming polymer is selected from the group consisting of polyethyleneimine, polylysine, polyvinyl alcohols, poly(hydroxyethyl (meth)acrylate), hydroxyallcylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, and polyamidoamines.

16. The method according to claim 1, wherein the organosulphur groups bear functions capable of reacting together so as to form around the fiber, during evaporation of the medium, a layer of crosslinked material.

17. The method according to claim 16, wherein the functions capable of reacting together are selected from the group consisting of alkoxysilanes, halosilanes, siloxanes, thiols, acrylic and vinyl double bonds.

18. The method according to claim 1, wherein the organomodified metallic nanoparticles are coated with an organic polymer.

19. The method according to claim 18, wherein the organic polymer is adsorbed onto the surface of the nanoparticles.

20. The method according to claim 18, wherein the organic polymer is fixed via covalent bonding to the self-assembled organosulphur groups.

21. The method according to claim 1, wherein the nanoparticles have a core/shell structure with a metallic shell surrounding a core, the material of the core being other than a metal in elemental form.

22. The method according to claim 21, wherein the material forming the core is a mineral material selected from the group consisting of the oxides, oxide dihydrates, hydroxides, carbonates, sulphides, silicates and phosphates of silicon, calcium, magnesium, zinc, aluminium, titanium, zirconium or cerium, micas and nacres.

23. The method according to claim 21, wherein the material forming the core is an organic polymer selected from the group consisting of styrene homopolymers and copolymers, polyorganosiloxanes, fluoro polymers, copolymers of ethylene and of vinyl acetate, polyvinyl alcohols, poly(ethylene oxide), polyvinylpyrrolidone, homopolymers and copolymers based on (meth)acrylic acid andlor on alkyl (meth)acrylates, polyurethanes, polyamides, polycarbonates, poly(vinyl chloride), poly(vinyl acetate), polypropylene, polyethylene, polyisobutylene, poly(1-butenylene), cellulose ethers, organic esters of cellulose, carboxyalkylcelluloses, cellulose sulphates, dextran sulphates and dextran ethers.

24. The method according to claim 1, wherein the nanoparticles have a spherical, lamellar, fibrillar or random shape.

25. The method according to claim 1, wherein the metallic nanoparticles have a mean size of between 1 nm and 500 nm.

26. The method according to claim 1, wherein the metallic nanoparticles are modified by grafting groups that absorb visible or UV light, which are derivatives of organic dyes selected from the group consisting of nitrobenzene dyes, aminobenzene dyes, azo dyes, naphthoquinone, benzoquinone or anthraquinone dyes, aromatic diamine dyes, aminophenols, phenolic and naphtholic dyes, porphyrins, phthalocyanins, carotenoids, flavonoids, fluorescein, rhodamine and coumarin.

27. The method according to claim 1, wherein said suspension of organomodified metallic nanoparticles are applied before or after an oxidation dyeing, reducing, bleaching, permanent-waving, styling or straightening treatment.

28. A composition comprising, in a cosmetically acceptable medium, water, at least one cosmetic active principle, and organomodified metallic nanoparticles bearing a self-assembled monolayer of organosulphur groups on a surface thereof, wherein the metallic portion is selected from the group consisting of gold, silver, palladium, platinum, cadmium, and alloys of these metals.

29. The composition according to claim 28, comprising from 0.0001% to 50% by weight of organomodified metallic nanoparticles based on total weight.

30. The composition according to claim 28, wherein the at least one cosmetic active principle is selected from the group consisting of vitamins, saccharides, oligosaccharides, hydrolysed or non-hydrolysed, modified or unmodified polysaccharides, amino acids, oligopeptides, peptides, hydrolysed or non-hydrolysed, modified or unmodified proteins, polyamino acids, enzymes, branched or unbranched fatty acids and fatty alcohols, animal, plant or mineral waxes, ceramides and pseudoceramides, hydroxylated organic acids, UV screening agents, antioxidants and free-radical scavengers, chelating agents, antidandruff agents, seborrhoea regulators, calmants, cationic surfactants, cationic polymers, amphoteric polymers, optionally organo-modified silicones, mineral, plant or animal oils, polyisobutenes and poly($\alpha$-olefins), fatty esters, anionic polymers in dissolved or dispersed form, nonionic polymers in dissolved or dispersed form, reducing agents, hair dyes or pigments, and mixtures thereof.

31. The composition according to claim 28, comprising 0.001% to 50% by weight of cosmetic active principle relative to the total weight of the cosmetic composition.

\* \* \* \* \*